(12) United States Patent
Nelson

(10) Patent No.: US 7,572,260 B1
(45) Date of Patent: Aug. 11, 2009

(54) ORTHOPEDIC SURGICAL DEVICE FOR SIMULTANEOUS BONE REMOVAL ON BOTH SIDES OF A FIXATION PIN

(76) Inventor: Chris L. Nelson, 9797 Sidehill Rd., North East, PA (US) 16428

( * ) Notice: Subject to any disclaimer, the term of this patent is extended or adjusted under 35 U.S.C. 154(b) by 200 days.

(21) Appl. No.: 11/145,156

(22) Filed: Jun. 6, 2005

(51) Int. Cl.
*A61B 17/00* (2006.01)
(52) U.S. Cl. ........................................................ 606/85
(58) Field of Classification Search ............. 606/80–85; 451/356; 407/29.1, 29.11, 29.14, 29.15; 76/24.1, 31, 101.1, 119
See application file for complete search history.

(56) References Cited

U.S. PATENT DOCUMENTS

| | | | | |
|---|---|---|---|---|
| 3,467,100 | A | 9/1969 | Rubin | 128/305 |
| 3,815,599 | A * | 6/1974 | Deyerle | 606/85 |
| 4,625,725 | A | 12/1986 | Davison et al. | 128/304 |
| 4,739,750 | A * | 4/1988 | Masse et al. | 606/85 |
| D304,372 | S | 10/1989 | Berry, Jr. | D24/147 |
| 5,006,121 | A | 4/1991 | Hafeli | 307/106 |
| D324,424 | S | 3/1992 | Michelson | D24/147 |
| D338,528 | S | 8/1993 | Koros et al. | D24/146 |
| 5,342,365 | A | 8/1994 | Waldman | 606/85 |
| 5,620,448 | A | 4/1997 | Puddu | 606/87 |
| 5,707,276 | A | 1/1998 | Holko et al. | 451/356 |
| 6,048,345 | A * | 4/2000 | Berke et al. | 606/85 |
| 6,120,508 | A | 9/2000 | Grunig et al. | 606/85 |
| 6,436,101 | B1 * | 8/2002 | Hamada | 606/85 |
| 6,537,280 | B2 * | 3/2003 | Dinger et al. | 606/85 |
| 2002/0138078 | A1 * | 9/2002 | Chappuis | 606/85 |
| 2004/0024405 | A1 * | 2/2004 | Lee | 606/82 |

FOREIGN PATENT DOCUMENTS

| | | |
|---|---|---|
| JP | 09 284791 A | 4/1996 |
| JP | 2000 125225 A | 10/1998 |
| JP | 2005 092075 | 9/2003 |

\* cited by examiner

*Primary Examiner*—Eduardo C Robert
*Assistant Examiner*—Michael J Araj
(74) *Attorney, Agent, or Firm*—Wayne L. Lovercheck

(57) ABSTRACT

A slotted bone rasp for reciprocal planing of opposed bone surfaces joined by a fixation pin so that the bone surfaces are made congruous and parallel to each other preparatory to bone fusion irrespective of pin orientation includes a shank with a pair of legs defining a slot for accommodating the pin and the legs having a flat side and an opposed abrasive side for remodeling the bone surfaces. Each leg includes an inner opposed convex surface whereupon the slot is narrowest at its midline so that the rasp is laterally pivotal transverse to the pin axis providing oblique angulations of the plane of bone removal relative to the pin axis; and the rasp also being rotatable to at least 90 degrees arc of rotation about the pin for 360 degree coverage of the bone surface creating two parallel bone surfaces in maximal end-to-end contact for successful bone fusion.

6 Claims, 3 Drawing Sheets

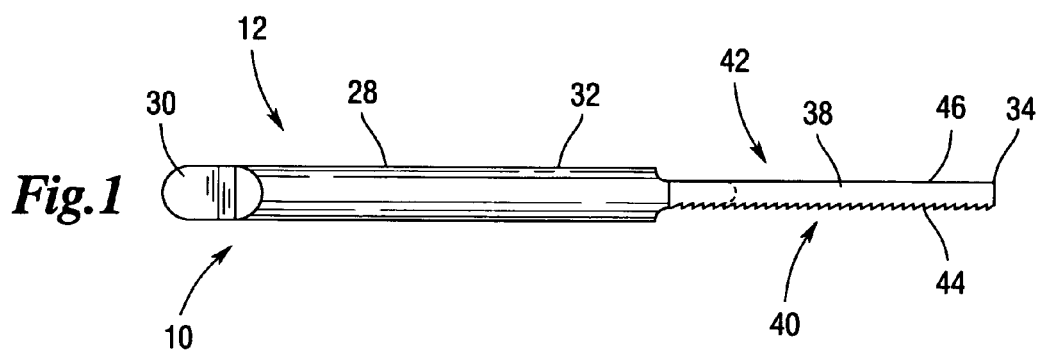
*Fig.1*
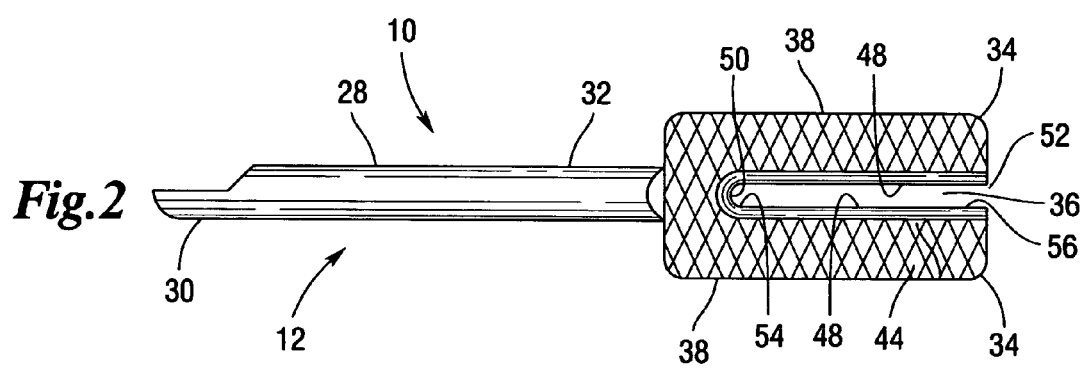
*Fig.2*
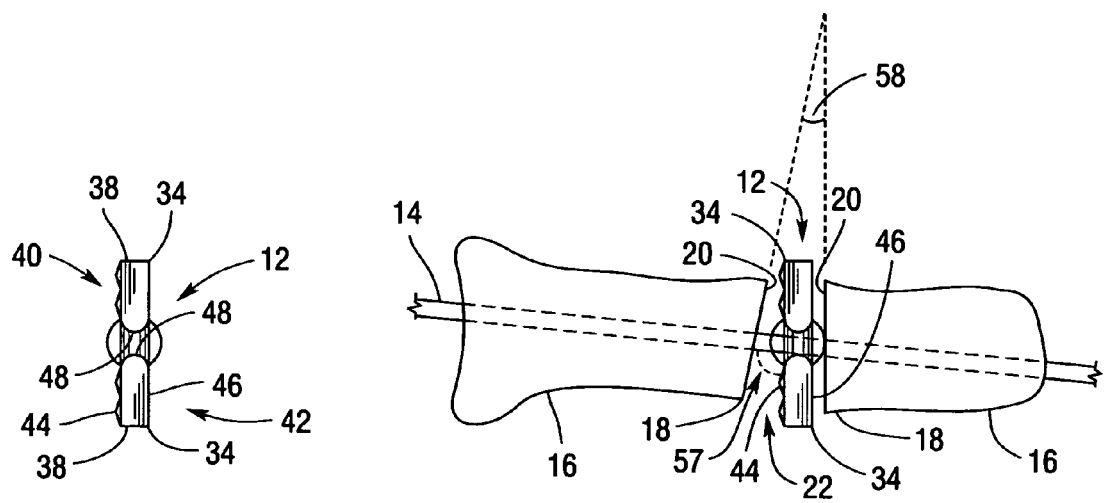
*Fig.3*          *Fig.4*

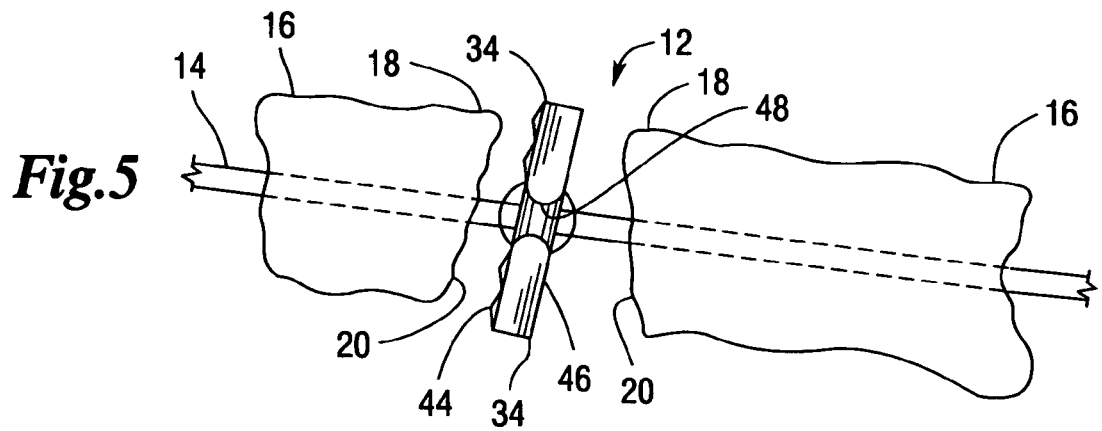
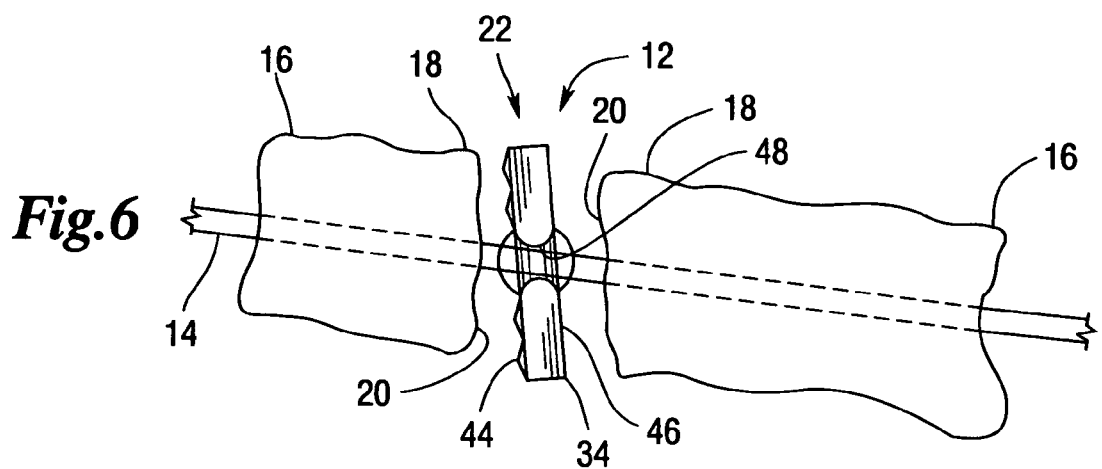
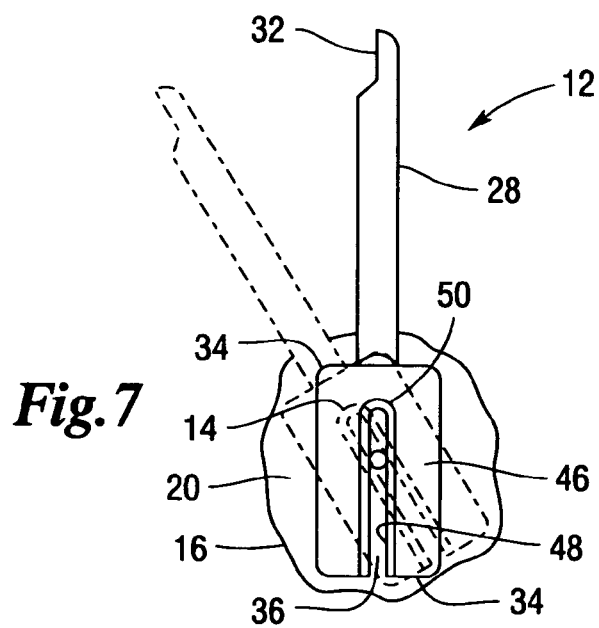

ORTHOPEDIC SURGICAL DEVICE FOR SIMULTANEOUS BONE REMOVAL ON BOTH SIDES OF A FIXATION PIN

FIELD OF THE INVENTION

The present invention pertains to orthopedic surgical devices, and more particularly pertains to a slotted bone rasp for simultaneously removing bone on both sides of a fixation pin with the bone rasp working between the opposed end surfaces of two adjacent bones joined by the fixation pin for creating two parallel and congruous bone surfaces preparatory for bone fusion.

BACKGROUND OF THE INVENTION

Bone rasps are commonly used in orthopedic surgery, especially in surgery involving the phalangeal, metatarsal or metacarpal bones, as part of the process of bone fusion. Many orthopedic surgeries such as osteotomy and arthrodesis procedures involve the use of a bone rasp. Under certain circumstances, a type of device, such as an internal fixation pin (an intramedullary pin), is inserted into the ends of the opposed bones, bone portions or bone fragments as part of such procedures referred to as interphalangeal or metatarsophalangeal arthrodesis—arthrodesis being the surgical immobilization of a joint so that the bones can grow solidly together. Generally, once the fixation pin has been placed within the ends of adjacent bones, the pin cannot be redirected, i.e., its orientation cannot change; and the pin is often oblique to the adjacent end surface of one or both bones—the end surfaces of the bones defining the arthrodesis site and plane of fusion where the ends of the bones are adjoined. It is often the case that the bone surfaces at the ends of both bones are irregular and/or not congruent or located in parallel planes—a condition that hinders and often prevents the successful fusion of the bone surfaces so that the bones will not grow solidly together (non-union).

Therefore, bone reduction and remodeling must be carried out by the bone rasp upon the two opposed, irregular and non-planar bone surfaces, with one or both bone surfaces possibly being oblique to the axis of the internal fixation pin that joins and stabilizes the ends of the bones. However, conventional rasps have several critical shortcomings in so far as they do not allow for the simultaneous removal of bone from the bone surface on both sides of the intramedullary (internal fixation) pin during such procedures as interphalangeal or metatarsophalangeal arthrodesis. Moreover, a conventional bone rasp does not provide for a rapid, accurate and efficient method to address and overcome this surgical dilemma. This results in a notoriously high rate of non-union (the failure of the contiguous, end-to-end growth together of the bones at the end surfaces) in conventional end-to-end arthrodesis procedures, and improvement is desirable with the appropriate refinement of the instrumentation, i.e., an improved bone rasp. Improvements in the bone rasp should provide for a more accurate reduction—surgical bone remodeling—of the opposed end surfaces of the bones for achieving optimal congruity between the bone surfaces while maintaining bone stabilization and relative orientation via the in situ internal fixation pin. Also, the improved bone rasp should decrease the operative time and, thereby, the rate of non-union, that is the failure of the end surfaces of both bones to join and fuse in an end-to-end, parallel and contiguous configuration.

The prior art discloses a variety of orthopedic devices, rasps, and abraders for shaping and forming various bones and bone structures as part of various types of surgical procedures.

For example, the Rubin patent (U.S. Pat. No. 3,467,100) discloses a nasal osteotome that includes a handle from which two legs extend, one of which is pointed and the other having a plane end surface for striking with a hammer or other tool.

The Davison et al. patent (U.S. Pat. No. 4,625,725) discloses a surgical rasp for cosmetic or facial surgery and includes a handle and an insert with a geometric tooth pattern arranged thereon.

The Berry Jr. patent (U.S. Des. Pat. 304,372) discloses on ornamental design for a surgical bone rasp that includes a handle and an attached serrated portion.

The Hafeli patent (U.S. Pat. No. 5,006,121) discloses a bone broach that prepares a bone for an implant and includes a mandrel on which a plurality of broach plates are stacked with each plate having a peripheral region that defines a cutting edge for making the desired bone opening.

The Michelson patent (U.S. Des. Pat. 324,424) discloses an ornamental design for a spinal osteotome that includes a handle and a serrated portion attached thereto with the serrated portion having a plurality of spaced-apart apertures disposed along the body of the serrated portion.

The Koros et al. patent (U.S. Des. Pat. 338,528) discloses an ornamental design for a flexible hip prosthesis osteotome that includes a round handle from which a flat file-shaped portion projects in axial alignment with the handle.

The Waldman patent (U.S. Pat. No. 5,342,365) discloses a rasp for plastic and reconstructive surgery that includes a handle having an insert with teeth arranged on the insert in parallel rows relative to the longitudinal axis of the handle.

The Puddu patent (U.S. Pat. No. 5,620,448) discloses a bone plate system for performing tibial or femoral osteotomies and which includes a forked-wedge tool for opening a wedge in the bone and a set of bone plates for maintaining the wedge opening.

The Holko et al. patent (U.S. Pat. No. 5,707,276) discloses an abrader blade having an abrasive surface and a pair of opposed depth control wings for controlling the depth of the shape that is abraded into the hard object such as bone tissue.

The Grunig et al. patent (U.S. Pat. No. 6,120,508) discloses a rasp that includes a handle adapter to which is mounted an inner support unit. Mounted on the inner support unit is a toothed exterior envelope of metal or surgical steel and which can be discarded after use.

The Chappuis Patent Application (U.S. Publication No. US2002/0138078 A1) discloses a system and method for facilitating bone grafting and which includes a rasp, a sizer, a cutting guide, a measuring pan and a holding device.

Nonetheless, despite the ingenuity of the above systems, methods and devices, there remains a need for an orthopedic device that is capable of working around a fixation pin for rapid and optimal remodeling of the irregular end surfaces of two opposed bones stabilized by the fixation pin where the end surfaces of the bones are non-parallel and/or oblique to the axis of the fixation pin and that can simultaneously reduce and remodel bone located at end surfaces on either side of the fixation pin.

SUMMARY OF THE INVENTION

The present invention comprehends an orthopedic surgical device in the form of a slotted or split rasp that is used for the reciprocal planing of one or both bone surfaces at the ends of adjacent bones that are adjoined by a non-threaded internal fixation pin. The slotted rasp is utilized to insure that the bone surfaces are made parallel and congruous irrespective of the irregularity of the bone surfaces and their non-perpendicularity relative to the pin axis so that the bone surfaces can be brought into contiguous, end-to-end alignment and contact for successful bone fusion.

The slotted rasp includes a shank that can be attached to a handle or hand piece of, for example, a reciprocating power instrument that mechanically reciprocates the rasp for planing of the bone surfaces. Diverging from the lower end of the shank is a pair of legs, bilateral in configuration, with the legs spaced from each other to form a slot extending therebetween. The slot accommodates the fixation pin, and can both slide and pivot about and on the pin. The legs include a unitary smooth surface and an opposite unitary abrasive surface that engages the bone surfaces for bone reduction and remodeling. Each leg includes an inner curvature of variable radius in the form of an inner convex surface with the slot being narrowest at its midline and the slot coaxial with the shank. The slot also includes two rounded corners at its closed end and two rounded corners at its mouth or open end. In operation the rasp can be rotated up to at least 90 degrees (45 degrees to either side of and) about the axis of the fixation pin thereby covering 360 degrees of bone surface at the end of each bone; and, in addition, the inner convex surfaces that define the slot allow the abrading surfaces of the rasp to pivot and achieve an angle non perpendicular to the longitudinal axis of the pin for efficient and rapid bone removal and remodeling so that the end surfaces of both bones are made parallel and congruent to each other in preparation for the end-to-end fusion of the opposed bone surfaces.

It is an objective of the present invention to provide an orthopedic surgical device in the form of a slotted bone rasp that allows for the accurate removal of bone from the end surfaces of adjacent bones so that the end surfaces are made coplanar with each other for proper fusing and joining of the end surfaces while maintaining the fixation pin in position.

It is another objective of the present invention to provide an orthopedic surgical device in the form of a slotted bone rasp that allows for the simultaneous removal of bone from both sides of the fixation pin that joins the two opposed bones adjacent their end surfaces.

It is yet another objective of the present invention to provide an orthopedic surgical device in the form of a slotted bone rasp that allows bone remodeling to be carried out on two non co-planar bone surfaces one or both of which may be oblique to the axis of the longitudinally placed intramedullary fixation pin joining the opposed ends of the bones.

It is still yet another objective of the present invention to provide an orthopedic surgical device in the form of a slotted bone rasp that allows bone remodeling of the bone surfaces to be carried out in a rapid, efficient and accurate manner.

It is still yet a further objective of the present invention to provide an orthopedic surgical device in the form of slotted bone rasp that allows for the more accurate reduction of the opposed bone surfaces to corresponding parallel surfaces without disturbing the disposition of the fixation pin that joins the ends of the bones adjacent their opposed surfaces.

Still another objective of the present invention is to provide an orthopedic surgical device in the form of a slotted bone rasp that is able to work about an arc of rotation around the fixation pin that joins the ends of the bones thereby allowing bone remodeling and planing by the rasp to cover 360 degrees of the entire end surface of each bone.

Still yet a further objective of the present invention is to provide an orthopedic surgical device in the form of a slotted bone rasp that is pivotal at least up to 90 degrees about the axis of the fixation pin for the rapid and efficient creation of two parallel bone surfaces with minimal bone trauma and thermonecrosis.

Still yet another objective of the present invention is to provide an orthopedic surgical device in the form of a slotted bone rasp wherein the rasp can be pivoted about the axis of the fixation pin for effecting the rapid and efficient creation of parallel bone surfaces at the opposed ends of both bones joined together by the fixation pin.

Still yet a further objective of the present invention is to provide an orthopedic surgical device in the form of a slotted bone rasp wherein the width of the slot can be varied to accommodate fixation pins of various sizes and diameters.

A further objective of the present invention is to provide an orthopedic surgical device in the form of a slotted bone rasp wherein the overall width of the rasp measured from the outside surface of the legs is variable and is based upon the size of the arthrodesis/fusion site.

A still yet further objective of the present invention is to provide an orthopedic surgical device in the form of a slotted bone rasp that can be toggled or pivoted lateral and transverse to the axis of the fixation pin because of the convex radius on the inner surfaces of the slot that allows for angulation of the plane of bone removal relative to the longitudinal axis of the fixation pin that joins the ends of the bones.

Another objective of the present invention is to provide an orthopedic surgical device in the form of a slotted bone rasp whose use allows for maximal or complete bone-to-bone contact of the opposed bone surfaces so that the contiguous, end-to-end growth and fusion of the bones at their end surfaces results.

Yet another objective is to provide an orthopedic surgical device in the form of a slotted bone rasp wherein a set of bone rasps can be provided with each bone rasp sized and dimensioned for a particular use and anatomic site.

These and other objects, features and advantages will become apparent to one skilled in the art upon a perusal of the following detailed description read in conjunction with the accompanying drawing figures and appended claims.

BRIEF DESCRIPTION OF THE DRAWINGS

FIG. 1 is a side elevational view of the orthopedic surgical device in the form of a slotted bone rasp illustrating the smooth side of the bone rasp and the abrasive side of the bone rasp;

FIG. 2 is a front elevational view of the orthopedic surgical device in the form of the slotted bone rasp illustrating the abrasive side of the bone rasp that engages the end surfaces of the bones for bone reduction and remodeling;

FIG. 3 is a bottom plan view of the orthopedic surgical device in the form of the slotted bone rasp illustrating the opposed convex inner surfaces of the legs that define the slot;

FIG. 4 is a side elevational view of the orthopedic surgical device in the form of the slotted bone rasp illustrating two bone portions joined by an internal fixation pin with the end surface of one bone portion being irregular and non-congruent to the opposite smooth end surface of the other bone portion;

FIG. 5 is a side elevational view of the orthopedic surgical device in the form of the slotted bone rasp illustrating two bone portions joined by the fixation pin with their end surfaces irregular and non-congruent to each other and the bone rasp pivoted laterally and transverse to the fixation pin;

FIG. 6 is a side elevational view of the orthopedic surgical device in the form of the slotted bone rasp illustrating two bone portions joined by the fixation pin with their end surfaces irregular and non-congruent to each other and the bone rasp pivoted laterally and transverse to the fixation pin opposite of the pivotal orientation of the bone rasp as shown in FIG. 4;

FIG. 7 is an end view of the orthopedic surgical device in the form of the slotted bone rasp illustrating the rotation of the slotted bone rasp about the fixation pin.

DETAILED DESCRIPTION OF THE PREFERRED EMBODIMENT

Figure 8:
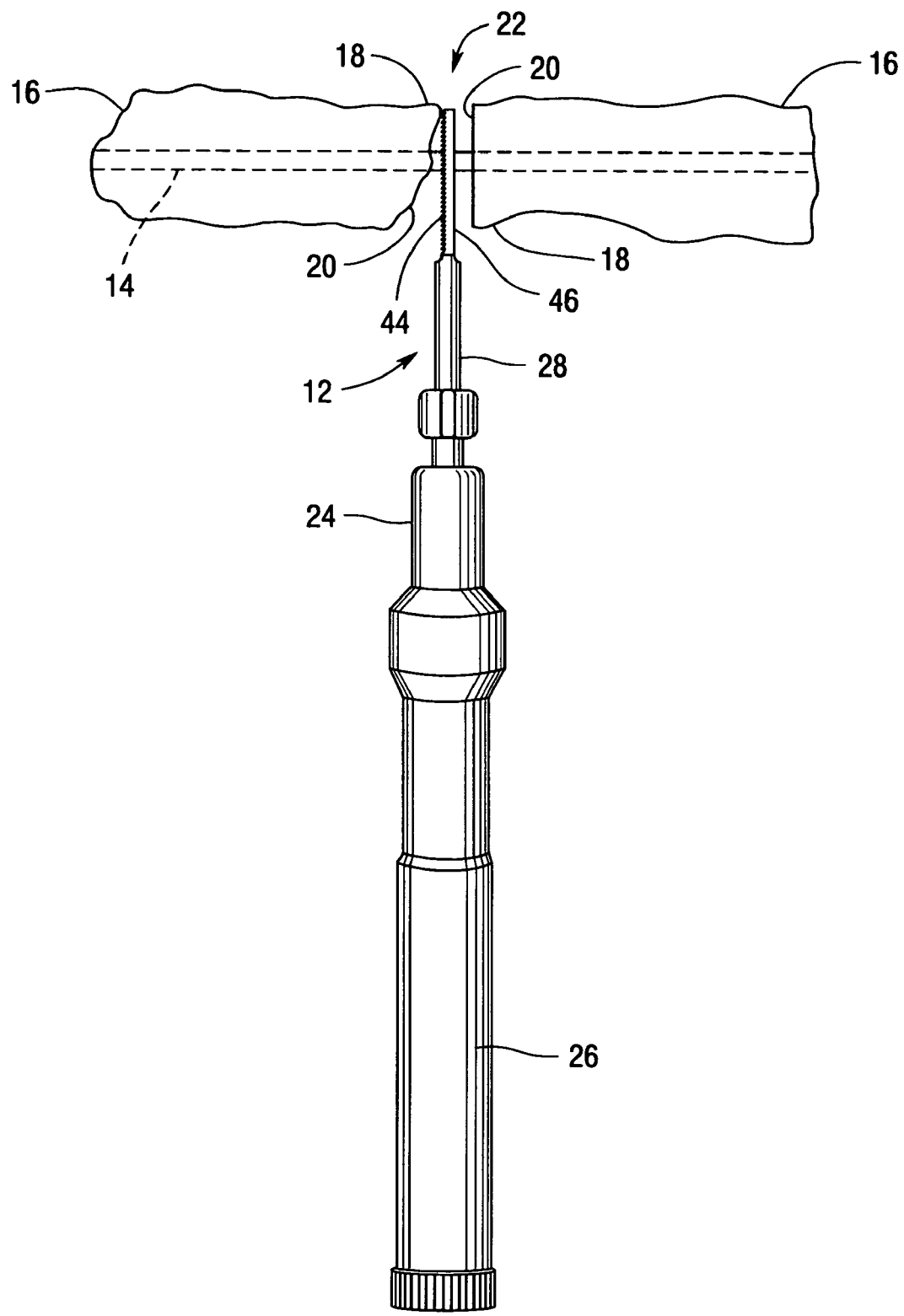
FIG. 8 is an elevational view of the orthopedic surgical device in the form of the slotted bone rasp illustrating the attachment of the bone rasp to a reciprocating power tool.

Illustrated in FIGS. 1 through 8 is an orthopedic surgical device 10 for use in such procedures as interphalangeal or metatarsophalangeal arthrodesis. Specifically, orthopedic surgical device 10 is a slotted, split or forked-shaped bone rasp 12 that is able to work around an already-placed internal fixation pin whereby bone rasp 12 is capable of reciprocal planing of bone surfaces preparatory to bone fusion.

As shown in FIGS. 4 through 8 for illustrative and representative purposes, an intramedullary fixation pin 14 has been inserted into two adjacent bones 16 that can be portions or segments of bones such as the phalangeal, metatarsal or metacarpal bones, for joining and maintaining the alignment of bones 16. Each bone 16 includes a bone end 18 that defines an end surface 20 and slotted rasp 12 is inserted between end surfaces 20 and slid onto pin 14 for the arthrodesis procedure as will be hereinafter further described. The area that includes and extends between end surfaces 20 of bones 16 is referred to as the fusion or arthrodesis site 22. End surfaces 20, which may also be referred to as the arthrodesis surfaces, are often not necessarily perpendicular to intramedullary fixation pin 14. Moreover, because of the fracture, oblique surgical plane of resection, or break that has occurred at proposed arthrodesis site 22, end surfaces 20 (the arthrodesis surfaces) of bones 16 are irregular, noncongruent and/or non-parallel with each other. Since fixation pin 14 is fixed in its longitudinal orientation and cannot be reoriented or redirected, it is end surfaces 20 of bones 16 that must be remodeled so they are made parallel and congruous to each other for 100 percent end surface 20 to end surface 20 contact so that successful fusion of the end surfaces 20 of bones 16 can result thus allowing bones 16 themselves to grow solidly together as part of the recuperative, healing process. Although it is possible for bone reduction and remodeling of end surfaces 20 to be accomplished manually by slotted rasp 12, mechanical means are more often employed to accomplish rapid and efficient bone remodeling results; thus, for example, slotted rasp 12 is attachable and detachable to handle 24 of a reciprocating power tool 26 as shown in FIG. 8, to effect bone reduction and remodeling.

As shown in FIGS. 1, 2, 7 and 8, slotted bone rasp 12 includes an elongated, generally cylindrical-shaped shank 28. Shank 28 includes a tool attachment end 30 and an opposite lower end 32. Tool attachment end 30 is stepped or indented in order to facilitate the easy and quick attachment to and detachment from power tool 26. Diverging from lower end 32 of shank 28, and integrally attached thereto, is a pair of tines, furcations or legs 34 that are coequal in length. Legs 34 are spaced from each other thereby creating an internal slot 36 for receiving pin 14 so that bone rasp 12 can rotationally, pivotally and reciprocally move on and about pin 14, and against end surfaces 20, to effect bone reduction and remodeling on one or possibly both end surfaces 20. As shown in FIG. 2, each leg 34 includes a smooth exterior or outer surface 38, and the distance from outside surface 38 of one leg 34 to outside surface 38 of the other leg 34 defines an overall width for bone rasp 12. Shank 28 defines a longitudinal axis that, in effect, bisects legs 34 and slot 36, and as will become apparent, legs 34 are bilateral in configuration. Moreover, legs 34 are integrally joined to each other and have an elongated and exaggerated U-shape configuration as shown in FIG. 2.

As shown in FIGS. 1 through 8, legs 34 include a working bone engagement side 40 and an opposite flat side 42. Specifically, working side 40 of legs 34 includes a surface 44 having abrasive, cross-cut, or serrated elements, teeth, or ridges that contact and engage end surfaces 20 of bones 16 for planing and physically reducing and remodeling end surfaces 20. Flat side 42 of legs 34 further defines a smooth surface 46 and, thus, when abrasive surface 44 engages one end surface 20 during the arthrodesis procedure, the opposite smooth surface 46 of legs 34 is placed against and slides upon the opposite end surface 20 but does not reduce or remodel that end surface 20.

The shape and configuration of slot 36 includes features that enhance the operation of bone rasp 12, i.e., the pivotal, rotational and lateral movement of bone rasp 12 on and about fixation pin 14 and relative to fixation pin 14 so that the entire end surfaces 20 of bones 16 can be fully remodeled as needed for producing two congruent and parallel bone surfaces suitable for fusion. Specifically, each leg 34 includes a curved inner convex surface of constant or variable radius (constant radius is shown in the drawings) 48 with inner convex surface 48 of one leg 34 opposing or facing the inner convex surface 48 and similarly shaped, surface 48 of the other leg 34 and thus, in part, creating slot 36 with convex surfaces 48 being coequal in length with slot 36. Slot 36 is thus narrowest at its mid-line (where the convex inner surfaces are closest to each other), and the mid-line of slot 34 is concentric with the axis of shank 28. In addition, slot 36 includes an inner end 50 and an opposite mouth or open end 52. Inner end 50 is further defined by opposed rounded inside corners 54 each of which is congruent or commensurate with that portion of inner convex surface 48 adjacent inner end 50. In addition, slot 36 includes two rounded outside corners 56 each of which is congruent or commensurate with that portion of the respective inner convex surface 48 adjacent the open or mouth end 52 of slot 36.

It should be noted that the width of slot 36 as measured, for example, from the longitudinal peak of one inner convex surface 48 to the peak of the opposite inner convex surface 48 is variable—or can be varied—for accommodating fixation pins 14 of different diameters. In addition, the overall width of rasp 12 as measured from outer surface 38 of one leg 34 to the outer surface 38 of the other leg 34 is variable based upon the dimensions—the width—of arthrodesis/fusion site 22. Furthermore, the length of slot 36 and the length of rasp 12 are variable to accommodate the specific type of hand piece or tool and the depth of arthrodesis site 22.

As illustrated in FIGS. 4 through 8, slotted bone rasp 12 is shown in various orientations relative to end surfaces 20 of bones 16 and the orientation of fixation pin 14 joining bone ends 18 of each bone 16. In FIG. 4 one end surface 20 is planar from the action of abrasive surface 44 of rasp 12, or from prior utilization of a power saw, while the other end surface 20 is irregular and non congruous to smooth end surface 20, and therefore fusion of end surfaces 20 can't occur until the irregular surface is remodeled so that end surface 20 can be made congruous and parallel with the already remodeled end surface 20. FIGS. 5 and 6 illustrate the ability of rasp 12 to toggle or pivot laterally and transversely on fixation pin 14 and relative to the longitudinal axis of fixation pin 14. Thus, when abrasive surface 44 of rasp 12 is brought against irregular end surface 20 of bone portion 16, the plane in which bone removal occurs is oblique to the axis or longitudinal extension of fixation pin 14. The convexity of inner surfaces 48 of legs 34 allow legs 34 to laterally pivot away from perpendicular relative to pin 14 so that the plane of bone removal is adjustable to various oblique (angle 57) angulations as the surgical geometry (angle 58) dictates. If inner surfaces 48 of legs 34 were flat then the lateral and pivotal movement of legs 34 relative to pin 14 would be prohibited, and abrasive surface 44 would have difficulty reaching—or would be completely unable to reach—various configurations of irregular end surfaces thereby impeding and preventing the bone planing and remodeling process.

FIG. 7 illustrates the ability of rasp 12 to rotate on and about fixation pin 14 for covering the full end surface 20 at end 18 of bone 16. While it is conceivable that rasp 12 would need to be rotated 360 degrees completely about fixation pin 14, in general the entire end surfaces 20 of bones 16 can be covered—planed and remodeled—by a 90-degree or less rotation of rasp 12. For illustrative purposes rasp 12 has been rotated approximately 30 degrees on pin 14 relative to the initial position of rasp 12. FIG. 7 also shows that the reciprocal planing of end surface 20 occurs on both sides of fixation pin 14 as abrasive surface 44 equally covers both legs 34 and one leg 34 is on one side of pin 14 while the other leg 34 is positioned on the other side of pin 14. In FIG. 8, rasp 12 is shown attached to handle 24 of reciprocating power tool 26 with pin 14 enclosed by slot 36 and between convex surfaces 48. Abrasive surface 44 of both legs 34 faces irregular end surface 20 while smooth surface 46 of both legs 34 is adjacent and will slide against the smooth remodeled end surface 20 that is perpendicular to fixation pin 14. It should be noted that the irregularity and non-congruity of the end surfaces 20 of the bones 16 is widely variable, and the irregularity and non-congruity of end surfaces 20 shown in FIGS. 4 through 8 are illustrative of the many different irregular, non-congruous shapes or configurations that may occur. In addition, the planing and remodeling of end surface 20 of one bone 16 so that surface 20 is made parallel and congruous with the other end surface 20 for fusion thereto can occur simultaneous with the lateral, pivotal movement of rasp 12, as illustrated in FIGS. 5 and 6, or simultaneous with the rotation of rasp 12 on pin 14, as illustrated in FIG. 7.

Although the present invention has been described in relation to a preferred embodiment, numerous alterations, variations, and modifications will become apparent to those skilled in the art without departing from the spirit of the invention or the scope of the appended claims.

What is claimed is:

1. An orthopedic bone rasp device for complete planing of the end surfaces of a pair of bones that are joined together by a fixation pin are made parallel, planar, and congruous to each other in preparation for their fusion together, comprising:

an elongated shank for removable attachment to a reciprocating power tool;
a pair of legs extending from and integrally attached to the shank with the legs being spaced from each other;
the legs including a smooth surface and an opposite working side with the working side including an abrasive surface that is dimensioned for acting upon a substantially large percentage of the substrate area of the end surfaces of the pairs of bones with the working side contoured to avoid marginal and peripheral splintering of the end surfaces of the bones;
each leg including an inner convex surface of variable radius shaped and oriented at an angle that is not perpendicular to the adjacent abrasive and smooth surfaces and the inner convex surfaces being disposed in a parallel orientation with respect to each other;
the inner convex surfaces being spaced from each other for defining a slot; and
whereupon the slot slides on the fixation pin with the fixation pin being accommodated within the slot defined by the inner convex surfaces of the legs so that the legs are located on opposite sides of the fixation pin with the legs capable of rotating at least 180 degrees about the fixation pin and capable of toggling and laterally pivoting on the fixation pin at various degrees of obliquity relative to the axis of the fixation pin for reciprocally and simultaneously planing the entire end surface of each bone on both sides of the fixation pin so that the end surfaces of both bones are made congruently planar and parallel to each other and able to be brought into complete apposition in preparation for the fusion together of the end surfaces of the bones.

2. The orthopedic bone rasp device of claim 1 wherein the abrasive surface is dimensioned for acting upon more than 50 percent of the substrate area of the end surfaces of the pairs of bones.

3. The orthopedic bone rasp device of claim 1 wherein the inner convex surfaces of each leg permits the legs to pivot away from perpendicular and to a state of obliquity relative to the longitudinal extension of the fixation pin with the legs simultaneously maintaining contact with opposing sides of the fixation pin as the fixation pin intersects with and emerges from the respective end surfaces of the bones during the process of end surface planing.

4. The orthopedic hone rasp device of claim 3 wherein the abrasive surfaces of the legs simultaneously and completely plane on both sides of the fixation pin up to and about the entire circumference of the fixation pin on the end surface of one bone while the smooth surfaces of the legs are oriented to and ride against the end surface of the opposed bone thereby insuring that the end surface of the opposed bone is maintained parallel irrespective of the oblique orientation of the fixation pin relative to the bones.

5. The orthopedic bone rasp device of claim 4 wherein the legs are capable of rotation about the fixation pin at least up to 90 degrees in the clockwise direction and the counterclockwise direction relative to the longitudinal extension of the fixation pin thereby allowing the legs to access and reshape the complete end surface of each bone.

6. The orthopedic bone rasp device of claim 5 wherein the legs are capable of toggling and laterally pivoting away from perpendicular with respect to the longitudinal orientation of the fixation pin so that the planing of the end surface of each bone occurs at angulations that are oblique with respect to the axis of the fixation pin thereby allowing the end surfaces of each bone to be made congruous, parallel and capably reshaped resulting in the complete apposition of the end surfaces to each other across their entire surface area while maintaining the fixation pin in situ throughout the entire remodeling process.

* * * * *